United States Patent [19]

Rochat

[11] Patent Number: 5,792,133
[45] Date of Patent: Aug. 11, 1998

[54] FLEXIBLE FILTERING POUCH

[75] Inventor: Jean-Denis Rochat, Genolier, Switzerland

[73] Assignee: Medtronic Electromedics, Inc., Parker, Colo.

[21] Appl. No.: 731,572

[22] Filed: Oct. 16, 1996

[30] Foreign Application Priority Data

Oct. 26, 1995 [CH] Switzerland ............... 3052/95

[51] Int. Cl.$^6$ .................. A61B 19/00; A61M 5/14
[52] U.S. Cl. .................. 604/406; 604/408; 604/410
[58] Field of Search .................. 604/405, 406, 604/408, 410, 4, DIG. 24

[56] References Cited

U.S. PATENT DOCUMENTS

| | | | |
|---|---|---|---|
| 4,033,345 | 7/1977 | Sorenson et al. | 604/406 |
| 4,235,233 | 11/1980 | Mouwne | 604/406 |
| 4,356,012 | 10/1982 | Hofstetter | 604/405 |
| 4,573,992 | 3/1986 | Marx | 604/408 |
| 4,642,088 | 2/1987 | Gunter | 604/4 |
| 4,734,269 | 3/1988 | Clarke et al. | 604/405 |
| 4,810,376 | 3/1989 | Magasi | 604/410 |
| 4,983,102 | 1/1991 | Swain | 417/394 |
| 5,269,924 | 12/1993 | Rochat . | |
| 5,573,526 | 11/1996 | Hess | 604/408 |

FOREIGN PATENT DOCUMENTS

| | | |
|---|---|---|
| 0 206 638 | 12/1986 | European Pat. Off. . |
| 0 484 751 | 5/1992 | European Pat. Off. . |
| 0 525 493 | 2/1993 | European Pat. Off. . |
| 0 645 151 | 3/1995 | European Pat. Off. . |

Primary Examiner—Robert A. Clarke
Assistant Examiner—David J. Cho
Attorney, Agent, or Firm—Young & Thompson

[57] ABSTRACT

The disposable flexible pouch for collecting and filtering blood has two inner chambers separated from each other by a filtering screen (11), a first chamber being connected to the outside by an outlet opening for the filtered blood and a second chamber being connected to the outside by an inlet opening for the blood to be processed. The pouch is formed from two superposed walls (1, 2) made of a flexible plastic material and bonded together by welding of their respective peripheral edges (3). The inlet and the outlet openings for the blood, as well as an outlet opening (5) for the suction air provided with a bacterial filter, are all made in the same wall (2) forming the pouch and the filtering screen (11) having a lower surface at the surface of this same wall (2) cooperates with the inner face thereof to form several compartments communicating with one another and forming the second chamber, so that the retention volume is reduced.

6 Claims, 3 Drawing Sheets

FLEXIBLE FILTERING POUCH

FIELD OF THE INVENTION

The present invention is concerned with a disposable flexible filtering pouch, in particular for use in an apparatus for collecting and filtering blood under sterile conditions, during and after an operation, for example of the type object of patent EP 0.525.493, filed by the present applicant.

BACKGROUND OF THE INVENTION

It actually appeared in practice that the disposable flexible pouch which is described in the above-mentioned document presents drawbacks arising from its structure and its manufacture. In particular, this pouch (for example as illustrated in FIG. 1 of patent EP 0.525.493) includes two chambers substantially of the same volume and separated from each other by an internal flexible filtering wall, for example made of polyester. Actually, this construction provides a first retention chamber for the blood to be filtered exhibiting a high volume between the inlet into said chamber and the filter, and a considerable amount of blood to be filtered accumulates rapidly in this first chamber between the external wall thereof and the internal filtering wall, even more so when the latter becomes clogged owing to the clotting of the blood collected, which also may contain solid particles. This relatively large retention volume is in practice disadvantageous on the one hand because the pressure difference between the two chambers driving the blood through the filter is decreased owing to the fact that the surface of the filter in contact with the blood to be filtered is relatively important and, on the other hand, because the volume retained cannot be recovered owing to the fact that it cannot be accessed to from the bottom of the pouch via the drainage located downstream of the filter.

SUMMARY OF THE INVENTION

Accordingly, the object of the present invention is to provide a disposable flexible filtering pouch, in particular for an apparatus for collecting and filtering blood, which does not suffer the above-mentioned drawbacks of known pouches.

The above-mentioned object is achieved by using a flexible filtering pouch object of the invention such as defined in claim 1.

BRIEF DESCRIPTION OF THE DRAWINGS

This invention shall now be described in more detail with reference to the annexed drawing illustrating schematically and by way of example an embodiment of the filtering pouch.

DETAILED DESCRIPTION OF THE INVENTION

Figure 1:
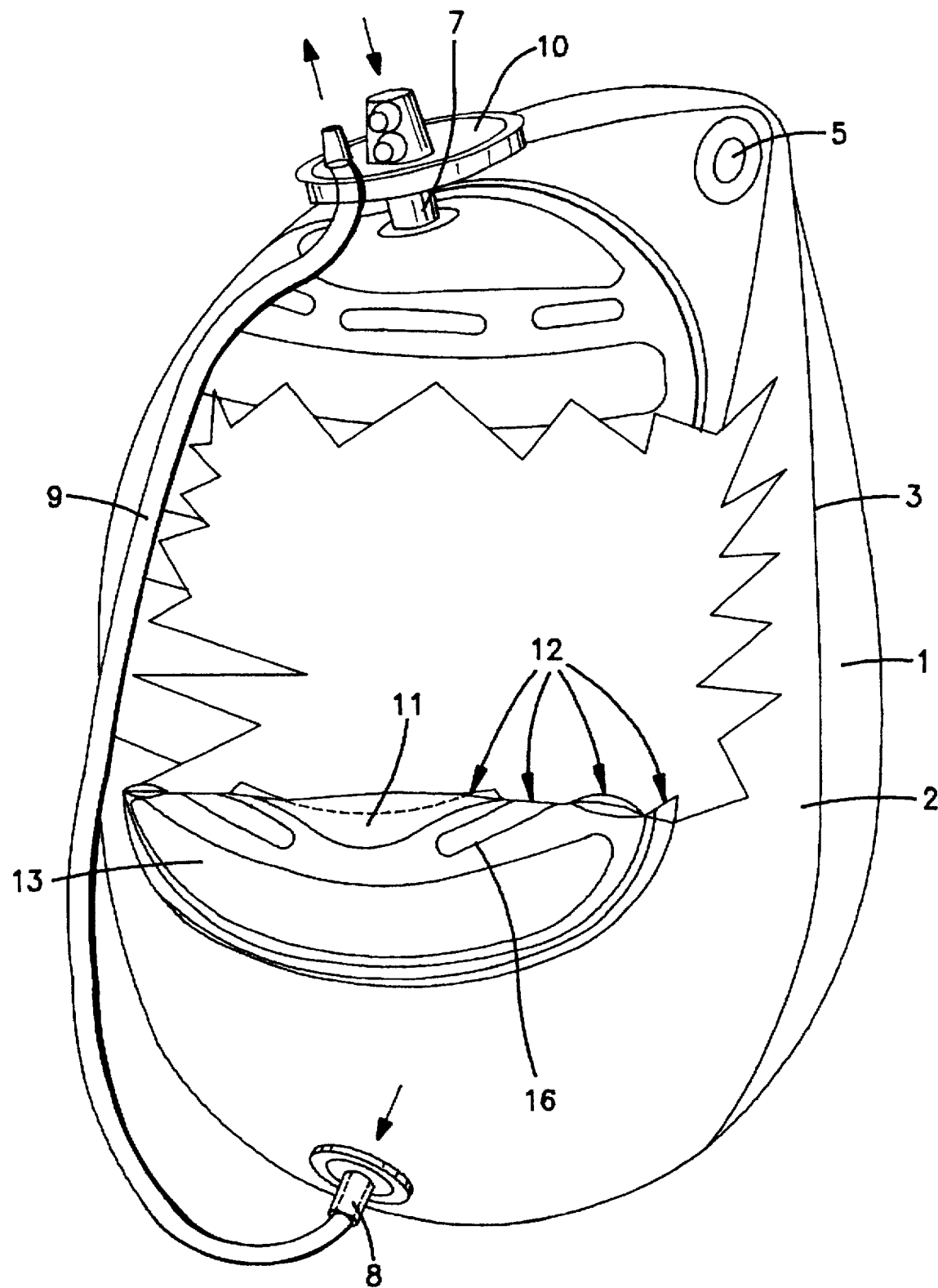
FIG. 1 is a general perspective partly exploded view
Figure 2:
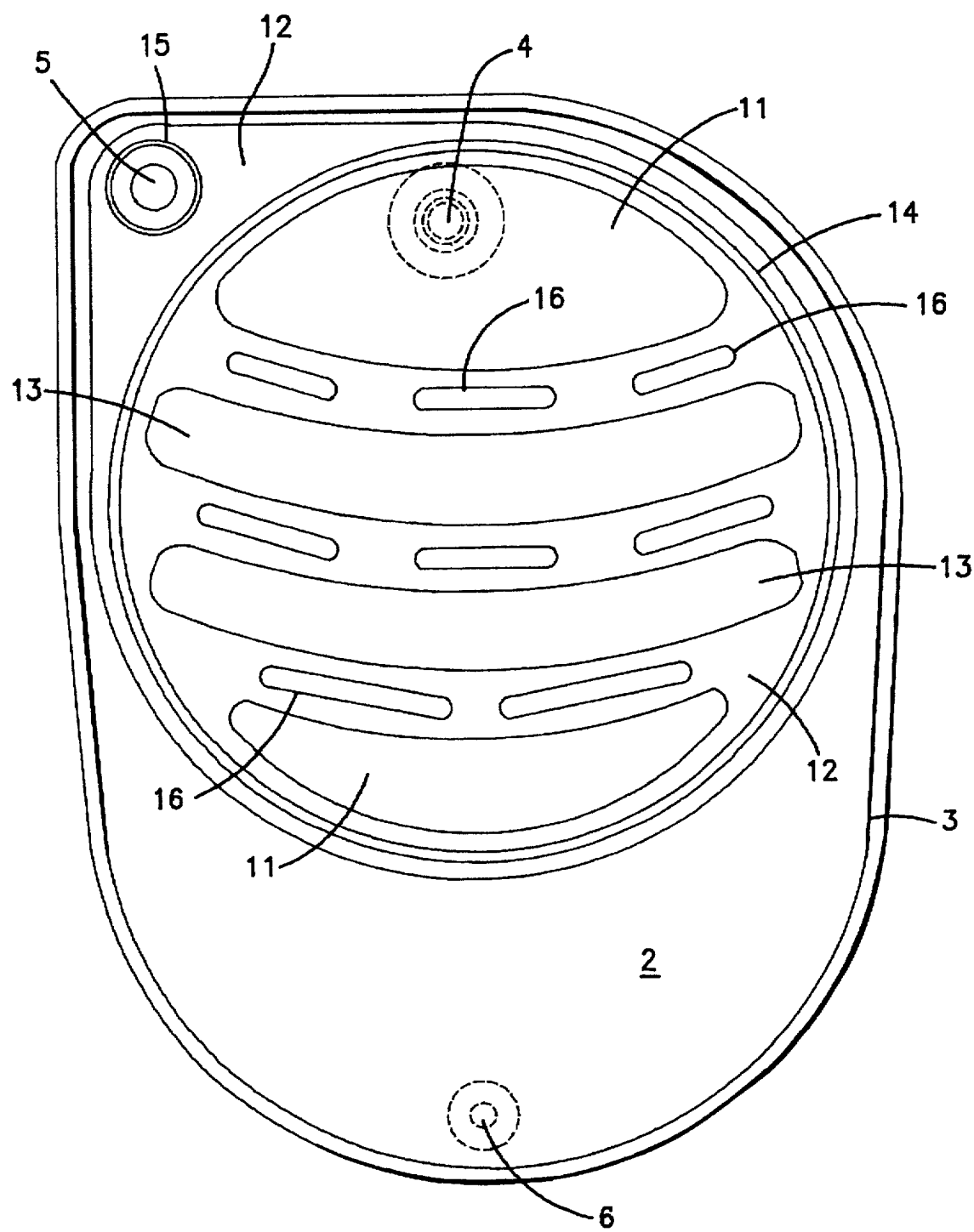
FIG. 2 is a plan view of one of the walls forming the pouch according to FIG. 1.
Figure 3:
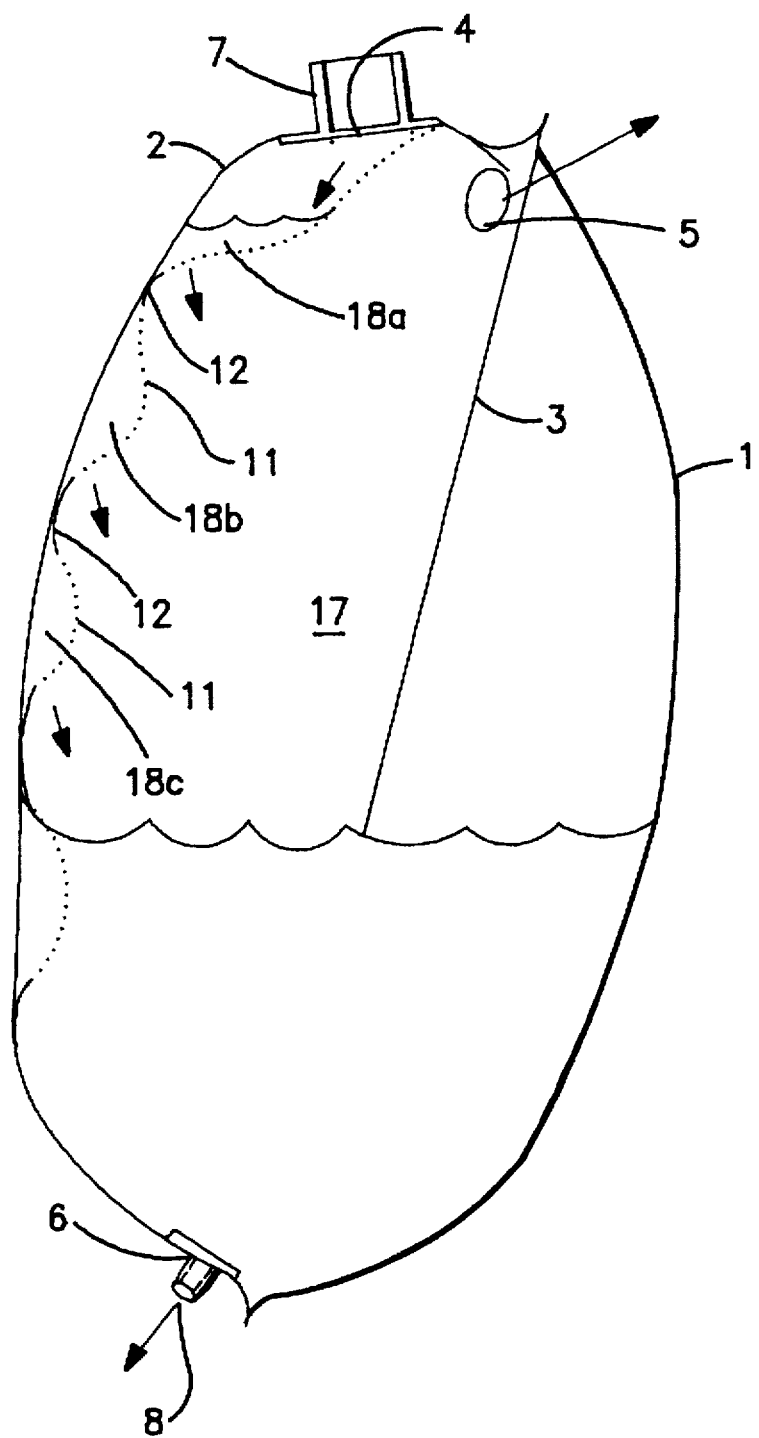
FIG. 3 is a schematic cross-sectional view illustrating the functioning of the pouch according to FIG. 1.

The embodiment of the flexible filtering pouch according to the invention as it is illustrated in FIGS. 1 to 3 is constructed in a manner known per se from two walls 1 and 2, preferably made of PVC, and assembled flat along their peripheral edges 3.

One of the walls 1 made of PVC is simple and does not have any opening, nor any additional component. Conversely, the other wall 2 made of PVC and as illustrated more particularly in FIG. 2 has three openings, namely a first opening 4 for the inflow of the raw blood to be processed and of the suction air, a second opening 5 situated as the first one in the upper part of the wall 2 and designed for the outflow of air and a third opening 6 situated in the lower part of the wall 2 for the outflow of the filtered blood. On the blood inlet opening 4 and on the blood outlet opening 6, there are bonded by welding to the PVC wall the respective connection tubes 7 and 8. The air outlet 5 is provided with a polypropylene screen having an electrostatic effect and acting as a bacterial filter.

As illustrated in FIG. 1, the connection tube 8 for the outflow of the filtered blood can be connected to an external drainage tubing 9, extending to a cap 10 which is also integral with the connection tube 7 for the inflow of the blood to be processed and of the suction air. This cap 10 is designed for cooperating sealingly in the active position with an apparatus for collecting and filtering blood (not illustrated), for example of the type described in the patent EP 0.525.493 filed by the present applicant.

On the other hand and as to the filtration itself, the wall 2 made of PVC having the above-mentioned openings 4, 5, 6 is provided on its inner face with a filtering screen 11, preferably made of polyester, having openings in the order of 20 to 500 μ, e. g. of about 150 μ. This filtering screen 11 is generally treated with heparin and made hydrophobic for reducing blood clotting.

The surface of the filter 11 is smaller than that of the wall 2 to which it is bonded. Owing to the fact that neither the polyester of filter 11, nor the polypropylene bacterial filter which is provided at the air outlet 5 are suitable for direct and simple welding to PVC, these two filter members are welded to the PVC wall via a counter-member 12 also made of PVC and placed so that the filter members be sandwiched between two layers of PVC, the welding being then carried out in a conventional manner using high frequency welding machines.

The counter-member 12 has an opening matching the opening of the outlet 5 for the suction air, as well as several elongated horizontal openings 13 intended to allow the passage of the filtered blood. More particularly, the PVC counter-member 12 is welded to the wall 2 (also made of PVC) while sandwiching the filtering screen 11, along a peripheral weld 14, with a substantially circular weld 15 being made around the air outlet opening 5. Horizontal weld islands 16 (see FIG. 2) are also provided for holding the filter 11 close to the wall 2.

The special positioning of the filtering screen 11 in relation to the wall 2 has the effect of creating, inside the flexible filtering pouch, a first chamber 17 of a volume which is relatively important and which is intended for receiving the filtered blood, as well as a second chamber of a total volume which is small by comparison with that of the first chamber 17, and which is actually formed of several compartments 18a, 18b and 18c, placed horizontally and communicating with one another, as illustrated schematically in FIG. 3. The opening 4 for the inflow of blood opens directly into the upper compartment 18a of the second chamber for receiving the blood to be processed.

Again referring to the schematic drawing of FIG. 3, the succession of operations in the filtration process is as follows. The disposable flexible filtering pouch must obviously be first placed in a suitable apparatus (not illustrated) and connected to a suction means and to a vacuum control means. The soiled blood (containing for example clotted blood, bone debris, etc.) to be filtered is fed by suction into the upper compartment 18a of the second chamber, via the inlet opening 4, and also by the effect of the suction caused by the vacuum produced by the apparatus, the blood flows across the filtering screen 11 into the first chamber 17, from which it can be pumped out via the outlet opening 6.

In an alternate version (not illustrated), the retention chamber formed of several communicating compartments 18a, 18b, 18c can be advantageously partly or totally filled with granules made of a plastic material (PVC), for example having a diameter of about 3 mm, in order to further reduce the retention volume, while bringing about a prefiltration effect. Such a prefiltration can be particularly useful for defibrinating blood before the same traverses the filtering screen 11 having openings of, for example, about 150 μ.

Thus, by comparison with the known flexible filtering pouches, for example of the type described in patent EP 0.525.493, the pouch according to the present invention makes it possible to remedy the drawbacks of the same:

the position of the filtering screen close to the wall makes it possible to restrict the retention volume of the blood;

because of this, should the filter start becoming blocked, the pressure differential across the filter would increase very rapidly and the filter could then be unblocked, with the result that the operation of the apparatus is made more reliable;

the outlay of the weld islands makes it possible to increase the maximum pressure at which the filter would burst because of a partial blocking of the filter;

the manufacturing is considerably facilitated owing to the fact that all the openings and the additional components (in particular the filter) are provided on only one of the two constituent walls;

finally, an external drainage tubing avoids certain drawbacks of an internal tubing.

I claim:

1. A disposable flexible pouch for collecting and filtering blood, having two inner chambers separated from each other by a filtering screen, a first chamber being connected to the outside by an outlet opening for filtered blood and a second chamber being connected to the outside by an inlet opening for raw blood to be processed, said pouch being formed by a first wall and a second wall, said two walls being made of a flexible plastic material, placed one upon the other and bonded by welding of their respective peripheral edges, wherein the inlet opening for the raw blood, the outlet opening for the purified blood, as well as a suction air outlet opening which is provided with a bacterial filter, are all provided in the same first wall of the pouch, and the filtering screen having a surface which is smaller than the surface of said first wall, attaches with the inner face of said first wall, to form several compartments communicating with one another and forming said second chamber, so that the retention volume is reduced.

2. The flexible pouch according to claim 1, wherein the filtering screen is bonded to the inner face of said first wall by a counter-member made of a plastic material and exhibiting elongated openings which are substantially horizontal.

3. The flexible pouch according to claim 2, wherein the filtering screen is bonded to said first wall by a peripheral weld between said first wall and the counter-member, as well as by weld islands which are substantially horizontal and which define the communicating compartments.

4. The flexible pouch according to claim 3, wherein the bacterial filter is bonded at the suction air outlet opening by a peripheral weld surrounding a corresponding opening made in the counter-member.

5. The flexible pouch according to claim 1, wherein the communicating compartments forming said second chamber are at least partly filled with granules made of a plastic material.

6. The flexible pouch according the claim 1, further comprising an external drainage tubing connecting the outlet opening for the filtered blood to an upper part of the pouch.

* * * * *